US008753817B2

(12) United States Patent
Sun et al.

(10) Patent No.: US 8,753,817 B2
(45) Date of Patent: *Jun. 17, 2014

(54) CYSTIC FIBROSIS TRANSMEMBRANE CONDUCTANCE REGULATOR GENE MUTATIONS

(75) Inventors: Weimin Sun, Irvine, CA (US); Matthew J. McGinniss, San Diego, CA (US); Donghui Huang, San Ramon, CA (US); Arlene Buller, Rancho Santa Margarita, CA (US); Raymond Fenwick, Laguna Niguel, CA (US); Mei Peng, Irvine, CA (US); Franklin Quan, Rancho Santa Margarita, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/358,322

(22) Filed: Jan. 25, 2012

(65) Prior Publication Data

US 2012/0141996 A1 Jun. 7, 2012

Related U.S. Application Data

(62) Division of application No. 12/847,960, filed on Jul. 30, 2010, now Pat. No. 8,124,345, which is a division of application No. 11/938,138, filed on Nov. 9, 2007, now Pat. No. 7,820,388, which is a division of application No. 11/615,645, filed on Dec. 22, 2006, now Pat. No. 7,794,937.

(51) Int. Cl.
*C12Q 1/68* (2006.01)
*C12P 19/34* (2006.01)
*C07H 21/02* (2006.01)

(52) U.S. Cl.
USPC ................ 435/6.11; 435/91.1; 536/23.1

(58) Field of Classification Search
None
See application file for complete search history.

(56) References Cited

U.S. PATENT DOCUMENTS

| | | | |
|---|---|---|---|
| 4,683,194 A | 7/1987 | Saiki et al. | |
| 4,683,202 A | 7/1987 | Mullis | |
| 4,956,778 A | 9/1990 | Naito | |
| 4,998,617 A | 3/1991 | Ladd et al. | |
| 5,130,238 A | 7/1992 | Malek et al. | |
| 5,169,766 A | 12/1992 | Schuster et al. | |
| 5,846,710 A | 12/1998 | Bajaj | |
| 5,885,775 A | 3/1999 | Haff et al. | |
| 5,888,819 A | 3/1999 | Goelet et al. | |
| 5,955,377 A | 9/1999 | Maul et al. | |
| 5,981,178 A | 11/1999 | Tsui et al. | |
| 5,981,714 A | 11/1999 | Cheng et al. | |
| 6,011,588 A | 1/2000 | Kim | |
| 6,288,220 B1 | 9/2001 | Kambara et al. | |
| 6,355,429 B1 | 3/2002 | Nygren et al. | |
| 6,403,320 B1 | 6/2002 | Read et al. | |
| 6,406,844 B1 | 6/2002 | Pirrung et al. | |
| 6,812,339 B1 | 11/2004 | Venter et al. | |
| 2003/0235834 A1 | 12/2003 | Dunlop et al. | |
| 2004/0110138 A1 | 6/2004 | Lem et al. | |
| 2004/0126760 A1 | 7/2004 | Broude | |
| 2005/0059035 A1 | 3/2005 | Huang et al. | |
| 2008/0171332 A1 | 7/2008 | Sun et al. | |

FOREIGN PATENT DOCUMENTS

| | | |
|---|---|---|
| EP | 0 329 822 B1 | 6/1994 |
| EP | 0 237 362 B1 | 10/1998 |
| EP | 0 201 184 | 8/2004 |
| WO | WO-88/10315 | 12/1988 |
| WO | WO-89/06700 | 7/1989 |
| WO | WO-2004/040013 A1 | 5/2004 |

OTHER PUBLICATIONS

Weiss, Fu et al. Complete cystic fibrosis transmembrane conductance regulator gene sequencing in patients with idiopathic chronic pancreatitis and controls. 2005. Gut vol. 54:1456-1460.*
Accession No. AF205406,published on Apr. 16, 2004.
Accession No. AY183426,published on Jan. 27, 2003.
Audrézet, et al., "Genomic Rearrangements in the CFTR Gene: Extensive Allelic Heterogeneity and Diverse Mutational Mechanisms" Hum Mutat. 23(4):343-357 (2004).
Boat, et al., "The Metabolic Basis of Inherited Disease" Membrane Transport Systems, 6th ed, 2649-2680 (1989).
Carvalho-Oliveira, et al., "CFTR Localization in Native Airway Cells and Cell Lines Expressing Wild-type of F508del-CFTR by a Panel of Different Antibodies", Journal of Histochemistry & Cytochemistry, 52(2): 193-203, (2004).
Castellani et al, Consensus on the use and interpretation of cystic fibrosis mutation analysis in clinical practice, (2008), Journal of Cystic Fibrosis, vol. 7, pp. 179-196.
CF Genetic Analysis consortium newsletter #67 Jan. 5, 1996 http://www.genet.sickkids.on.ca/resource/nl.CFnewslet.67.html.
Chevalier-Porst et al, Identification of three rare frameshift mutations in exon 13 of the cystic fibrosis gene: 1918delGC, 2118del4 and 2372del8, Human Molecular Genetics, 2(7): 1071-1072, 1993.
Claass, et al., "Applicability of Different Antibodies for Immunohistochemical Localization of CFTR in Sweat Glands from Healthy Controls and from Patients with Cystic Fibrosis", The Journal of Histochemistry & Cytochemistry, 48(6): 831-837, (2000).
Cohn, et al., "CFTR: Development of High-Affinity Antibodies and Localization in Sweat Gland", Biochemical and Biophysical Research Communications, 181(1): 36-43, (1991).
Doucet, et al., "Applicability of Different Antibodies for the Immunohistochemical Localization of CFTR in Respiratory and Intestinal Tissues of Human and Murine Origin", 51(9): 1191-1199, (2003).

(Continued)

*Primary Examiner* — Amanda Haney
(74) *Attorney, Agent, or Firm* — Foley & Lardner LLP

(57) ABSTRACT

The present invention provides novel mutations of the CFTR gene related to cystic fibrosis or to conditions associated with cystic fibrosis. Also provided are probes for detecting the mutant sequences. Methods of identifying if an individual has a genotype containing one or more mutations in the CFTR gene are further provided.

26 Claims, 4 Drawing Sheets

(56) References Cited

OTHER PUBLICATIONS

Ezquieta et al, CF2603/4delT, a new frameshift mutation in exon 13 of the cystic fibrosis transmembrane conductance regulator (CFTR) gene. Human Genetics, 91:614-615, 1993.
Flanigan, et al., "Rapid Direct Sequence Analysis of the Dystrophin Gene", Am. J. Genet., 72:931-939, (2003).
Hantash, F. et al., Consultations in Molecular Diagnostics. Characterization of a Recurrent Novel Large Duplication in the Cystic Fibrosis Transmembrane Conductance Regulator Gene. The Journal of Molecular Diagnostics, vol. 9, No. 4, Sep. 2007, p. 556-560.
Hoogendoorn, et al., "Genotyping Single Nucleotide Polymorphisms by Primer Extension and High Performance Liquid Chromatography" Human Genetics 104:89-93 (1999).
Interview Summary dated Sep. 2, 2009 for U.S. Appl. No. 11/615,645.
Jenison, et al., "Use of a Thin Film Biosensor for Rapid Visual Detection of PCR Products in a Multiplex Format" Biosens Bioelectron 16(9-12):757-763 (2001).
Kwoh, et al, Proc. Natl. Acad. Sci., (1989), 86:1173-1177.
Landegren, et al., "A Ligase-Mediated Gene Detection Technique" Science 241:1077-1080 (1988).
Mendes, et al., "Antibodies in CFTR Studies", Journal of Cystic Fibrosis, 3: 69-72, (2004).
Newton, et al., "Analysis of any Point Mutation in DNA. The Amplification Refractory Mutation System (ARMS)" Nucleic Acids Res. 17:2503-2516 (1989).
Nickerson, et al., "Automated DNA Diagnostics Using an ELISA-Based Oligonucleotide Litigate Assay" Proc. Natl. Acad. Sci. USA 87:8923-8927 (1990).
Okayama, et al., "Rapid, nonradioactive detection of mutations in the human genome by allele-specific amplification", J. Lab. Clin. Med., 114:105-113, (1989).
Piggee, et al., "Capillary Electrophoresis for the Detection of Known Point Mutations by Single-Nucleotide Primer Extension and Laster-Induced Fluorescence Detection" Journal of Chromatography A 781:367-375 (1997).
Poddar, S.K., "Symmetric vs Asymmetric PCR and Molecular Beacon Probe in the Detection of a Target Gene of Adenovirus" Molec. and Cell. Probes 14:25-32 (2000).
Ratjen and Doring, Cystic Fibrosis, The Lancet, 361:681-689, 2003.
Romey et al, Two novel rare frameshift mutations (2423 del G in exon 13 and 1215 del G in exon 7) and one novel rare sequence variation (3271+18 C or T) identified in a patient with cystic fibrosis. Human Molecular Genetics, 3(6): 1003-1004, 1994.
Rowntree et al, The phenotypic consequences of CFTR mutations, 2003, Annals of Human Genetics, vol. 67, pp. 471-485.
Sarkar, et al., "Characterization of Polymerase Chain Reaction Amplification of Specific Alleles" Anal. Biochem. 186:64-68 (1990).
Sellner, et al., "MLPA and MAPH: New Techniques for Detection of Gene Deletions" Human Mutation 23:413-419 (2004).
Strom, et al., "Extensive sequencing of the cystic fibrosis transmembrane regulator gene: Assay validation and unexpected benefits of developing a comprehensive test", Genetics in Medicine, 5(1):9-14, (2003).
U.S. Final Office Action for U.S. Appl. No. 11/506,453 dated Jun. 6, 2008.
U.S. Notice of Allowance dated Nov. 13, 2009 for U.S. Appl. No. 11/615,645.
U.S. Office Action dated Mar. 9, 2009 for U.S. Appl. No. 11/938,138.
U.S. Office Action dated Jun. 13, 2008 for U.S. Appl. No. 11/615,645.
U.S. Office Action dated Jun. 26, 2009 for U.S. Appl. No. 11/615,645.
U.S. Office Action dated Aug. 8, 2007 for U.S. Appl. No. 11/506,453.
U.S. Office Action dated Oct. 31, 2007 for U.S. Appl. No. 11/506,453.
U.S. Office Action dated Nov. 24, 2008 for U.S. Appl. No. 11/615,645.
U.S. Office Action dated Dec. 11, 2008 for U.S. Appl. No. 11/506,453.
U.S. Office Action dated Jul. 7, 2009 for U.S. Appl. No. 11/938,138.
US Advisory Action dated May 10, 2010 in related U.S. Appl. No. 11/938,138.
US Notice of Allowance dated Apr. 26, 2010 in related U.S. Appl. No. 11/615,645.
US Notice of Allowance dated Jul. 9, 2010 in U.S. Appl. No. 11/938,138.
US Notice of Allowance dated Sep. 2, 2010 in U.S. Appl. No. 11/506,453.
US Office Action dated Sep. 16, 2009 in related U.S. Appl. No. 11/506,453.
US Office Action dated Apr. 2, 2010 in related U.S. Appl. No. 11/938,138.
US Office Action dated Jun. 15, 2011 in U.S. Appl. No. 12/847,960.
US Notice of Allowance dated Nov. 10, 2011 in U.S. Appl. No. 12/847,960.
Vankeerberghen et al, The cystic fibrosis transmembrane conductance regulator: an intriguing protein with pleiotropic functions, Journal of Cystic Fibrosis, 1:13-20, 2002.
Walker, et al., "Isothermal in Vitro Amplification of DNA by a Restriction Enzyme/DNA Polymerase System" Proc. Natl. Acad. Sci. USA 89:392-396 (1992).
Walker, et al., "Production and characterisation of monoclonal and polyclonal antibodies to different regions of the cystic fibrosis transmembrane conductance regulator (CFTR): detection of immunologically related proteins", Journal of Cell Science, (1995), 106:2433-2444.
Wall, et al. "A 31-Mutation Assay for Cystic Fibrosis Testing in the Clinical Molecular Diagnostics Laboratory" Human Mutation 5(4):333-338 (1995).
Weiss et al, Complete cystic fibrosis transmembrane conductance regular gene sequencing in patients with idiopathic chronic pancreatitis and controls, 2005, Gut vol. 54:1456-1460.
Welsh et al, Molecular mechanisms of CFTR chloride channel dysfunction in cystic fibrosis, Cell, 73: 1251-1254, 1993.
Wu, et al., "Allele-Specific Enzymatic Amplification of β-Globin Genomic DNA for Diagnosis of Sickle Cell Anemia" Proc. Natl. Acad. Sci. USA 86:2757-2760 (1989).
Zielenski, et al., "Genomic DNA Sequence of the Cystic Fibrosis Transmembrane Conductane Regulator (CFTR) Gene" Genomics 10:214-228 (1991).

* cited by examiner

Figure 1. Novel CFTR Mutations Identified from CF Sequencing

| Mutation | Location | Mutation Effect | Indication for Testing | Age | Gender | Other Mutation |
|---|---|---|---|---|---|---|
| 3443A>T | exon 17b | E1104V | adult onset cystic fibrosis (CF), diagnosed at 24, Caucasian | 40 | F | Delta F508 |
| 2443delA | exon 13 | Frameshift | positive immune reactive trypsinogen (IRT, 171.4 µg/L), sweat test (sodium 84 mEq/L, 86 mEq/L), (chloride 109 mEq/L, 109 mEq/L) stool elastase (44.8 µg/g). | 2 months | M | Delta F508 |
| 2777insTG | exon 14b | Frameshift | classic CF, sweat chloride value of 99 mEq/L | 3 months | M | None |
| 3123-3125delGTT | exon 17a | Deletion of L997 | CF patient; Hispanic ancestry; no other information available | | | 3791delC |
| 4177delG | exon 22 | frameshift | positive IRT, positive sweat test, failure to thrive (FTT) | 3 | M | 3007delG |
| 630delG | exon 5 | frameshift | family history, has child with CF who is heterozygous for G551D (from father) | 22 | F | none |
| 2068G>T | exon 13 | G646X | classic CF, had sibling who died at 11 months with CF | 7 months | M | Delta F508 |
| 1342-2A>G | intron 8 | splicing | classic CF | 37 | F | Delta F508 |
| 297-1G>A | intron 2 | splicing | positive IRT, positive sweat test | 52 days | F | Delta F508 |

Figure 1. Novel CFTR Mutations Identified from CF Sequencing (cont'd)

| Mutation | Location | Mutation Effect | Indication for Testing | Age | Gender | Other Mutation |
|---|---|---|---|---|---|---|
| 3500-2A>T | intron 17b | splicing | classic CF, Hispanic | 23 | M | R334W |
| 4375-2A>G | intron 23 | splicing | classic CF | 2 | M | 2184insA |
| 3172-3174delTAC | exon 17a | Deletion Y1014 | positive IRT, heterozygous for G542X | 48 days | NG | G542X |
| 2902G>C | exon 15 | D924H | positive IRT, negative mutation panel, negative sweat test | 5 months | M | none |
| 4115T>C | exon 22 | I1328T | atypical, borderline sweat test (54 mEq/L), recurrent pancreatitis, pneumonia | 13 | M | 1898+1G>A |
| 4185G>C | exon 22 | K1351N | atypical, sinusitis, pancreatitis | 21 | M | R117H, 5T/9T |
| 520C>G | exon 4 | L130V | 21 weeks pregnant, fetus has echogenic bowel | 25 | F | none |
| 842A>C | exon 6a | Q237P | positive sweat test, mild features suggestive of CF, heterozygous for 1 mutation | 11 | F | 621+1G>T |
| 4528G>T | exon 24 | A1466S | atypical, positive pseudomonas sputum, borderline sweat test | 6.5 years | M | c.3601-17 T>C |
| 448A>G | exon 4 | I106V | pancreatitis | 15 | M | 1716G>A |
| 574A>T | exon 4 | I148F | | 46 | F | Delta F508 |

Figure 1. Novel CFTR Mutations Identified from CF Sequencing (cont'd)

| Mutation | Location | Mutation Effect | Indication for Testing | Age | Gender | Other Mutation |
|---|---|---|---|---|---|---|
| 3704T>C | exon 19 | M1191T | | 4 | M | none |
| 1248+5T>C | intron 7 | | | 35 | F | R117H, 7T/7T |
| 296+12T>G | intron 2 | | child with possible CF | 32 | F | none |
| 3849+3G>A | intron 19 | | atypical, chronic cough, productive cough, central bronchectasia | 55 | F | none |
| 497A>G | exon 4 | Y122C | atypical, chronic constipation, poor weight gain, possible recurrent | 3 | M | none |
| -141C>A | promoter | | CF, pulmonary and pancreatic insufficient, infertile | 43 | M | none |
| 2875G>C | exon 15 | V915L | chronic cough, positive sweat test, pancreatic sufficient, suspicious of CF | 5.5 years | F | none |
| 2689A>G | exon 14a | I853V | | 16 months. | M | none |
| 3039A>G | exon 15 | A969A | congenital bilateral absence of the vas deferens (CBAVD), brother similarly affected. No other symptoms. | 38 | M | none |
| 405G>C | exon 3 | G91G (last | positive IRT | 1 month | M | 711+1G>T |

Figure 1. Novel CFTR Mutations Identified from CF Sequencing (cont'd)

| Mutation | Location | Mutation Effect (nucleotide) | Indication for Testing | Age | Gender | Other Mutation |
|---|---|---|---|---|---|---|
| 886G>A | exon 6b | A252T | borderline sweat test | 1.5 months | M | DF508, A309D |
| 4445G>A | exon 24 | R1438Q | No symptoms of CF; extensive sequencing ordered for infertility workup | not available | not available | none |
| -228G>C | promoter | | general population screen, mother tested positive during pregnancy | 2 months | M | Delta F508 |
| -295C>T | promoter | | chronic lung and growth disorder consistent with CF | 10 | F | none |
| -379delC | promoter | | possible CF, borderline sweat test, doing well on asthma medicines | 3.5 years | F | none |
| -540A>G | promoter | | atypical, recurrent cough, wheeze, chronic sinusitis | 9 | F | none |

CYSTIC FIBROSIS TRANSMEMBRANE CONDUCTANCE REGULATOR GENE MUTATIONS

CROSS-REFERENCE TO RELATED PATENT APPLICATIONS

This application is a divisional of U.S. application Ser. No. 12/847,960, filed Jul. 30, 2010 (now U.S. Pat. No. 8,124,345), Ser. No. 11/938,138, filed Nov. 9, 2007 (now U.S. Pat. No. 7,820,388), and Ser. No. 11/615,645, Filed Dec. 22, 2006 (now U.S. Pat. No. 7,794,937), each of which is incorporated by reference in its entirety.

FIELD OF THE INVENTION

The present invention relates to novel cystic fibrosis transmembrane regulator (CFTR) gene mutations and to methods for detecting the presence of these mutations in individuals.

BACKGROUND OF THE INVENTION

The following description of the background of the invention is provided simply as an aid in understanding the invention and is not admitted to describe or constitute prior art to the invention.

Cystic fibrosis (CF) is the most common severe autosomal recessive genetic disorder in the Caucasian population. It affects approximately 1 in 2,500 live births in North America (Boat et al., The Metabolic Basis of Inherited Disease, $6^{th}$ ed., pp 2649-2680, McGraw Hill, NY (1989)). Approximately 1 in 25 persons of northern European Caucasian descent are carriers of the disease. The responsible gene has been localized to a 250,000 base pair genomic sequence present on the long arm of chromosome 7. This sequence encodes a membrane-associated protein called the "cystic fibrosis transmembrane regulator" (or "CFTR"). There are greater than 1000 different mutations in the CFTR gene, each having varying frequencies of occurrence in different populations, presently reported to the Cystic Fibrosis Genetic Analysis Consortium. These mutations exist in both the coding regions (e.g., ΔF508, a mutation found on about 70% of CF alleles, represents a deletion of a phenylalanine at residue 508) and the non-coding regions (e.g., the 5T, 7T, and 9T variants correspond to a sequence of 5, 7, or 9 thymidine bases located at the splice branch/acceptor site of intron 8) of the CFTR gene.

The major symptoms of cystic fibrosis include chronic pulmonary disease, pancreatic exocrine insufficiency, and elevated sweat electrolyte levels. The symptoms are consistent with cystic fibrosis being an exocrine disorder. Although recent advances have been made in the analysis of ion transport across the apical membrane of the epithelium of CF patient cells, it is not clear that the abnormal regulation of chloride channels represents the primary defect in the disease.

A variety of CFTR gene mutations are known. The identification of additional mutations will further assist in the diagnosis of cystic fibrosis.

SUMMARY OF THE INVENTION

The inventors have discovered new mutations in the CFTR gene. These mutations, include 3443A>T, 2443delA (A at position 2443 is deleted), 2777insTG (TG are inserted at position 2777), 3123-3125delGTT (GTT at positions 3123-3125 are deleted), 4177delG (G at position 4177 is deleted), 630delG (G at position 630 is deleted), 2068G>T, 1342-2A>G (A in the splice acceptor site of intron 8, 2 nucleotides upstream of position 1342, is substituted with G), 297-1G>A (G in the splice acceptor site of intron 2, 1 nucleotide upstream of position 297, is substituted with A) 3500-2A>T (A in the splice acceptor site of intron 17b, 2 nucleotides upstream of position 3500, is substituted with T), 4375-2A>G (A in the splice acceptor site of intron 23, 2 nucleotides upstream of position 4375, is substituted with G), 3172-3174delTAC (TAC at positions 3172 to 3174 are deleted), 2902G>C, 4115T>C, 4185G>C, 520C>G, 842A>C, 4528G>T, 448A>G, 574A>T, 3704T>C, 1248+5T>C (T in the splice donor site of intron 7, 5 nucleotides downstream of position 1248, is substituted with C), 296+12T>G (T in intron 2, 12 nucleotides downstream of position 296, is substituted with G), 3849+3G>A (G in the splice donor site of intron 19, 3 nucleotides downstream of position 3849, is substituted with A), 497A>G, -141C>A, 2875G>C, 2689A>G, 3039A>G, 405G>C, 886G>A, 4445G>A, -228G>C, -295C>T, -379delC (C at position -379 is deleted), and -540A>G, are related to the function of the CFTR gene and, therefore, to cystic fibrosis. These mutations are associated with cystic fibrosis or are associated with conditions associated with cystic fibrosis. By "conditions associated with cystic fibrosis" is meant any clinical symptoms that may be found in a cystic fibrosis patient and are due to one or more CF mutations.

Accordingly, in one aspect, the present invention provides a method of determining if a CFTR gene contains one or more mutations selected from the group consisting of 3443A>T, 2443delA (A at position 2443 is deleted), 2777insTG (TG are inserted at position 2777), 3123-3125delGTT (GTT at positions 3123-3125 are deleted). 4177delG (G at position 4177 is deleted), 630delG (G at position 630 is deleted). 2068G>T, 1342-2A>G (A in the splice acceptor site of intron 8, 2 nucleotides upstream of position 1342, is substituted with G), 297-1G>A (G in the splice acceptor site of intron 2, 1 nucleotide upstream of position 297, is substituted with A) 3500-2A>T (A in the splice acceptor site of intron 17b, 2 nucleotides upstream of position 3500, is substituted with T), 4375-2A>G (A in the splice acceptor site of intron 23, 2 nucleotides upstream of position 4375, is substituted with G), 3172-3174delTAC (TAC at positions 3172 to 3174 are deleted), 2902G>C, 4115T>C, 4185G>C, 520C>G, 842A>C, 4528G>T, 448A>G, 574A>T, 3704T>C, 1248+5T>C (T in the splice donor site of intron 7, 5 nucleotides downstream of position 1248, is substituted with C), 296+12T>G (T in intron 2, 12 nucleotides downstream of position 296, is substituted with G), 3849+3G>A (G in the splice donor site of intron 19, 3 nucleotides downstream of position 3849, is substituted with A), 497A>G, -141C>A, 2875G>C, 2689A>G, 3039A>G, 405G>C, 886G>A, 4445G>A, -228G>C, -295C>T, -379delC (C at position -379 is deleted), and -540A>G, comprising determining whether CFTR nucleic acid contains one or more of said mutations.

In another aspect, the present invention provides a method of identifying if an individual has one or more mutations in the CFTR gene comprising determining if nucleic acid from the individual has one or more mutations in one or both CFTR genes, the mutations selected from the group consisting of 3443A>T, 2443delA (A at position 2443 is deleted), 2777insTG (TG are inserted at position 2777), 3123-3125delGTT (GTT at positions 3123-3125 are deleted), 4177delG (G at position 4177 is deleted), 630delG (G at position 630 is deleted), 2068G>T, 1342-2A>G (A in the splice acceptor site of intron 8, 2 nucleotides upstream of position 1342, is substituted with G), 297-1G>A (G in the splice acceptor site of intron 2, 1 nucleotide upstream of position 297, is substituted with A) 3500-2A>T (A in the splice acceptor site of intron 17b, 2 nucleotides upstream of position 3500, is substituted with T), 4375-2A>G (A in the splice acceptor site of intron 23, 2 nucleotides upstream of position 4375, is substituted with G), 3172-3174delTAC (TAC at positions 3172 to 3174 are deleted), 2902G>C, 4115T>C, 4185G>C, 520C>G, 842A>C, 4528G>T, 448A>G, 574A>T, 3704T>C, 1248+5T>C (T in the splice donor site of intron 7, 5 nucleotides downstream of position 1248, is substituted with C), 296+12T>G (T in intron 2, 12 nucleotides downstream of position 296, is substituted with G), 3849+3G>A (G in the splice donor site of intron 19, 3 nucleotides downstream of position 3849, is substituted with A), 497A>G, −141C>A, 2875G>C, 2689A>G, 3039A>G, 405G>C, 886G>A, 4445G>A, −228G>C, −295C>T, −379delC (C at position −379 is deleted), and −540A>G.

In yet another aspect, the present invention provides a method of determining if an individual is predisposed to cystic fibrosis or to a condition associated with cystic fibrosis comprising determining if nucleic acid from the individual has one or more mutations in one or both CFTR genes, the mutations selected from the group consisting of 3443A>T, 2443delA (A at position 2443 is deleted), 2777insTG (TG are inserted at position 2777), 3123-3125delGTT (GTT at positions 3123-3125 are deleted), 4177delG (G at position 4177 is deleted), 630delG (G at position 630 is deleted), 2068G>T, 1342-2A>G (A in the splice acceptor site of intron 8, 2 nucleotides upstream of position 1342, is substituted with G), 297-1G>A (G in the splice acceptor site of intron 2, 1 nucleotide upstream of position 297, is substituted with A) 3500-2A>T (A in the splice acceptor site of intron 17b, 2 nucleotides upstream of position 3500, is substituted with T), 4375-2A>G (A in the splice acceptor site of intron 23, 2 nucleotides upstream of position 4375, is substituted with G), 3172-3174delTAC (TAC at positions 3172 to 3174 are deleted), 2902G>C, 4115T>C, 4185G>C, 520C>G, 842A>C, 4528G>T, 448A>G, 574A>T, 3704T>C, 1248+5T>C (T in the splice donor site of intron 7, 5 nucleotides downstream of position 1248, is substituted with C), 296+12T>G (T in intron 2, 12 nucleotides downstream of position 296, is substituted with G), 3849+3G>A (G in the splice donor site of intron 19, 3 nucleotides downstream of position 3849, is substituted with A), 497A>G, −141C>A, 2875G>C, 2689A>G, 3039A>G, 405G>C, 886G>A, 4445G>A, −228G>C, −295C>T, −379delC (C at position −379 is deleted), and −540A>G.

In still a further aspect, the present invention provides a method of counseling an individual on the likelihood of having an offspring afflicted with cystic fibrosis or a condition associated with cystic fibrosis, comprising determining if nucleic acid from the individual has one or more mutations in one or both CFTR genes, the mutations selected from the group consisting of 3443A>T, 2443delA (A at position 2443 is deleted), 2777insTG (TG are inserted at position 2777), 3123-3125delGTT (GTT at positions 3123-3125 are deleted), 4177delG (G at position 4177 is deleted), 630delG (G at position 630 is deleted), 2068G>T, 1342-2A>G (A in the splice acceptor site of intron 8, 2 nucleotides upstream of position 1342, is substituted with G), 297-1G>A (0 in the splice acceptor site of intron 2, 1 nucleotide upstream of position 297, is substituted with A) 3500-2A>T (A in the splice acceptor site of intron 17b, 2 nucleotides upstream of position 3500, is substituted with T), 4375-2A>G (A in the splice acceptor site of intron 23, 2 nucleotides upstream of position 4375, is substituted with G), 3172-3174delTAC (TAC at positions 3172 to 3174 are deleted), 2902G>C, 4115T>C, 4185G>C, 520C>G, 842A>C, 4528G>T, 448A>G, 574A>T, 3704T>C, 1248+5T>C (T in the splice donor site of intron 7, 5 nucleotides downstream of position 1248, is substituted with C), 296+12T>G (T in intron 2, 12 nucleotides downstream of position 296, is substituted with G), 3849+3G>A (G in the splice donor site of intron 19, 3 nucleotides downstream of position 3849, is substituted with A), 497A>G, −141C>A, 2875G>C, 2689A>G, 3039A>G, 405G>C, 886G>A, 4445G>A, −228G>C, −295C>T, −379delC (C at position −379 is deleted), and −540A>G.

In some embodiments, the mutations are selected from the group consisting of 3443A>T, 2443delA (A at position 2443 is deleted), 2777insTG (TG are inserted at position 2777), 3123-3125delGTT (GTT at positions 3123-3125 are deleted), 4177delG (G at position 4177 is deleted), 630delG (G at position 630 is deleted), 2068G>T, 1342-2A>G (A in the splice acceptor site of intron 8, 2 nucleotides upstream of position 1342, is substituted with G), 297-1G>A (G in the splice acceptor site of intron 2, 1 nucleotide upstream of position 297, is substituted with A) 3500-2A>T (A in the splice acceptor site of intron 17b, 2 nucleotides upstream of position 3500 is substituted with T), 4375-2A>G (A in the splice acceptor site of intron 23, 2 nucleotides upstream of position 4375, is substituted with G), and 3172-3174delTAC (TAC at positions 3172 to 3174 are deleted). In other embodiments the mutations are selected from the group consisting of 2902G>C, 4115T>C, 4185G>C, 520C>G, 842A>C, 4528G>T, 448A>G, 574A>T, 3704T>C, 1248+5T>C (T in the splice donor site of intron 7, 5 nucleotides downstream of position 1248, is substituted with C), 296+12T>G (T in intron 2, 12 nucleotides downstream of position 296, is substituted with 0), 3849+3G>A (G in the splice donor site of intron 19, 3 nucleotides downstream of position 3849, is substituted with A), 497A>G, and −141C>A.

In some embodiments, one or more mutations are evaluated for both alleles of the CFTR gene in the individual. By this approach the genotype of the individual can be determined at the position of each mutation.

The presence of the mutation in the CFTR gene may be determined by any of a variety of well known methods used to detect single base changes (transitions, transversions, and/or small deletions/insertions). Thus, genomic DNA may be isolated from the individual and tested for the CF mutations. In another approach, mRNA can be isolated and tested for the CF mutations. Testing may be performed on mRNA or on a cDNA copy.

Genomic DNA or cDNA may be subject to amplification by the polymerase chain reaction or related methods using primers directed to specific portions of the CFTR gene which contain a mutation to be detected. The sequences of primers suitable for PCR amplification of portions of the CFTR gene in which contain the CF mutations are also provided.

The presence CF mutations can be determined in a nucleic acid by sequencing appropriate portions of the CFTR gene containing the mutations sought to be detected. For example, each amplicon of the CFTR gene is sequenced with both M13 forward and reverse primers. In another approach, CF mutations that change susceptibility to digestion by one or more endonuclease restriction enzymes may be used to detect the mutations. In another embodiment, the presence of one or more CF mutations can be determined by allele specific amplification. In yet another embodiment, the presence of one or more CF mutations can be determined by primer extension. In yet a further embodiment, the presence of one or more CF mutations can be determined by oligonucleotide ligation. In another embodiment, the presence of one or more CF mutations can be determined by hybridization with a detectably labeled probe containing the mutant CF sequence.

According to the invention, the presence of CF mutations can also be determined by analyzing the CF protein encoded by the mutated CF gene. The mutations include, for example, E1104V, deletion of L997, G646X, deletion of Y1014, D924H, I1328T, K1351N, L130V, Q237P, A1466S, I106V, I148F, M1191T, Y122C, V915L, I853V, A252T, R1438Q or frameshift mutations.

Detection of CF mutations at the protein level can be detected by any method well known in the field. In one embodiment, detection of CF mutations is carried out by isolating CF protein and subjecting it to amino acid sequence determination. This may require fragmenting the protein by proteolytic or chemical means prior to sequencing. Method of determining an amino acid sequence are well known in the art.

In other embodiments, the presence of CFTR mutations is determined using antibodies that bind specifically to a mutant CFTR protein sequence. For example, ELISA or other immunological assays known to a person skilled in the art can be used to detect CFTR mutations using specific antibodies for each mutation. Method of producing antibodies to specific sequence of a protein such as a mutation containing sequence are well known. For example, one may immunize an animal with the mutant CFTR protein or with peptide fragments of the mutant protein containing the mutant sequence. If monoclonal antibodies are produced, those specific for the mutant sequence can be obtained by screening the antibodies for differential reactivity between the mutant CFTR protein and wildtype CFTR protein. If a mutation specific polyclonal antisera is desired, one may process the initial antisera by removing antibodies reactive with the wildtype CFTR protein. Optionally, such antisera may be concentrated by affinity chromatography using the mutant CFTR protein. Further steps to remove wild-type CFTR reactivity may be conducted.

Methods for developing monoclonal and polyclonal antibodies to defined epitopes of the CFTR protein have been previously described. See, e.g., U.S. Pat. No. 5,981,714 (Cheng et al.); Cohn et al., Biochem Biophys Res Commun. 1991 Nov. 27; 181(1): 36-43; Walker et al, J Cell Sci. 1995 June; 108 (Pt 6): 2433-44; Klass et al. J Histochem Cytochem. 2000 June; 48(6): 831-7: Doucet et al., J Histochem Cytochem. 2003 September; 51(9): 1191-9; Carvelho-Oliveira et al. J Histochem Cytochem. 2004 February; 52(2): 193-203; and Mendes et al, J Cyst Fibros. 2004 August; 3 Suppl 2:69-72.

The methods of the invention also may include detection of other CF mutations which are known in the art and which are described herein.

The present invention also provides oligonucleotide probes that are useful for detecting the CF mutations. Accordingly, provided is a substantially purified nucleic acid comprising 8-20 nucleotides fully complementary to a segment of the CFTR gene that is fully complementary to a portion of the CFTR gene and encompasses a mutant CFTR sequence selected from the group consisting of 3443A>T. 2443delA (A at position 2443 is deleted), 2777insTG (TG are inserted at position 2777), 3123-3125delGTT (GTT at positions 3123-3125 are deleted), 4177delG (G at position 4177 is deleted), 630delG (G at position 630 is deleted). 2068G>T, 1342-2A>G (A in the splice acceptor site of intron 8, 2 nucleotides upstream of position 1342, is substituted with G), 297-1G>A (G in the splice acceptor site of intron 2, 1 nucleotide upstream of position 297, is substituted with A) 3500-2A>T (A in the splice acceptor site of intron 17b, 2 nucleotides upstream of position 3500, is substituted with T), 4375-2A>G (A in the splice acceptor site of intron 23, 2 nucleotides upstream of position 4375, is substituted with G), 3172-3174delTAC (TAC at positions 3172 to 3174 are deleted), 2902G>C, 4115T>C, 4185G>C, 520C>G, 842A>C, 4528G>T, 448A>G, 574A>T, 3704T>C, 1248+5T>C (T in the splice donor site of intron 7, 5 nucleotides downstream of position 1248, is substituted with C), 296+12T>G (T in intron 2, 12 nucleotides downstream of position 296, is substituted with G), 3849+3G>A (G in the splice donor site of intron 19, 3 nucleotides downstream of position 3849, is substituted with A), 497A>G, −141C>A, 2875G>C, 2689A>G, 3039A>G, 405G>C, 886G>A, 4445G>A, −228G>C, −295C>T, −379delC (C at position −379 is deleted), and −540A>G, or a complementary nucleic acid sequence thereof. In one embodiment, the purified nucleic acid is no more than 50 nucleotides in length. The invention CF mutant probes may be labeled with a detectable label, which may include any of a radioisotope, a dye, a fluorescent molecule, a hapten or a biotin molecule.

In another aspect the present invention provides kits for one of the methods described herein. In various embodiments, the kits contain one or more of the following components in an amount sufficient to perform a method on at least one sample: one or more primers of the present invention, one or more devices for performing the assay, which may include one or more probes that hybridize to a mutant CF nucleic acid sequence, and optionally contain buffers, enzymes, and reagents for performing a method of detecting a genotype of cystic fibrosis in a nucleic acid sample.

BRIEF DESCRIPTION OF THE DRAWINGS

FIG. 1 is a table showing various CFTR mutations and characterizing information. A normal immunoreactive trypsinogen (IRT) value is 30 μg/L, or lower. An elevated IRT value is an indication of possible CF condition. The normal range for a sweat test is a chloride value less than 40 mEq/L. An elevated chloride value is an indication of possible CF condition. A normal individual has a value of greater than 480 μg/g for a stool elastase test, while a value under 100 μg/g indicates severe pancreatic insufficiency.

DETAILED DESCRIPTION OF THE INVENTION

CF mutations and exemplary PCR primer pairs for amplifying segments of the CFTR gene containing the mutations are shown in Table 1.

TABLE 1

| CF mutations and associated amplification primers | | | | |
|---|---|---|---|---|
| CF Mutation Nucleotide Change | CF Mutation Nucleotide Change (HGVS nomenclature)* | CF Mutation Amino Acid Change | CF Mutation Amino Acid Change (HGVS nomenclature)* | Forward and Reverse PCR Amplification Primers |
| 3443A > T | c.3311A > T | E1104V | p.Glu1104Val | q17be1F (SEQ ID NO: 33) and q17be1R (SEQ ID NO: 34) |

TABLE 1-continued

CF mutations and associated amplification primers

| CF Mutation Nucleotide Change | CF Mutation Nucleotide Change (HGVS nomenclature)* | CF Mutation Amino Acid Change | CF Mutation Amino Acid Change (HGVS nomenclature)* | Forward and Reverse PCR Amplification Primers |
|---|---|---|---|---|
| 2443delA (A at position 2443 is deleted) | c.2311del | frameshift | p.Asn771fs | q13-2e1F (SEQ ID NO: 23) and q13-2e1R (SEQ ID NO: 24) |
| 2777insTG (TG are inserted at position 2777) | c.2644_2645dup | frameshift | p.Trp882fs | q14be2F (SEQ ID NO: 27) and q14be2R (SEQ ID NO: 28) |
| 3123-3125delGTT (GTT at positions 3123-3125 are deleted) | c.2991_2993del | deletion of L997 | p.Leu997del | q17ae1F (SEQ ID NO: 31) and q17ae1R (SEQ ID NO: 32) |
| 4177delG (G at position 4177 is deleted) | c.4045del | frameshift | p.Gly1349fs | q22e1F (SEQ ID NO: 39) and q22e1R (SEQ ID NO: 40) |
| 630delG (G at position 630 is deleted) | c.498del | frameshift | p.Lys166fs | g5e3F (SEQ ID NO: 11) and g5e4R (SEQ ID NO: 12) |
| 2068G > T | c.1936G > T | G646X | p.Gly646X | q13-1e1F (SEQ ID NO: 21) and q13-1e2R (SEQ ID NO: 22) |
| 1342-2A > G (A in the splice acceptor site of intron 8, 2 nucleotides upstream of position 1342, is substituted with G) | c.1210-2A > G | splicing | | g9e9F (SEQ ID NO: 19) and g9e11R (SEQ ID NO: 20) |
| 297-1G > A (G in the splice acceptor site of intron 2, 1 nucleotide upstream of position 297, is substituted with A) | c.165-1G > A | splicing | | s3e1F (SEQ ID NO: 7) and s3e2R (SEQ ID NO: 8) |
| 3500-2A > T (A in the splice acceptor site of intron 17b, 2 nucleotides upstream of position 3500, is substituted with T) | c.3368-2A > T | splicing | | q18e1F (SEQ ID NO: 35) and q18e1R (SEQ ID NO: 36) |
| 4375-2A > G (A in the splice acceptor site of intron 23, 2 nucleotides upstream of position 4375, is substituted with G) | c.4243-2A > G | splicing | | q24e1F (SEQ ID NO: 41) and q24e1R (SEQ ID NO: 42) |
| 3172-3174delTAC (TAC at positions 3172 to 3174 are deleted) | c.3040_3042del | deletion of Y1014 | p.Tyr1014del | q17ae1F (SEQ ID NO: 31) and q17ae1R (SEQ ID NO: 32) |
| 2902G > C | c.2770G > C | D924H | p.Asp924His | q15e3F (SEQ ID NO: 29) and q15e4R (SEQ ID NO: 30) |
| 4115T > C | c.3983T > C | I1328T | p.Ile1328Thr | q22e1F (SEQ ID NO: 39) and q22e1R (SEQ ID NO: 40) |
| 4185G > C | c.4053G > C | K1351N | p.Lys1351Asn | q22e1F (SEQ ID NO: 39) and q22e1R (SEQ ID NO: 40) |
| 520C > G | c.388C > G | L130V | p.Leu130Val | q4e1F (SEQ ID NO: 9) and q4e1R (SEQ ID NO: 10) |
| 842A > C | c.710A > C | Q237P | p.Gln237Pro | q6ae1F (SEQ ID NO: 13) and q6ae1R (SEQ ID NO: 14) |
| 4528G > T | c.4396G > T | A1466S | p.Ala1466Ser | q24e1F (SEQ ID NO: 41) and q24e1R (SEQ ID NO: 42) |
| 448A > G | c.316A > G | I106V | p.Ile106Val | q4e1F (SEQ ID NO: 9) and q4e1R (SEQ ID NO: 10) |

TABLE 1-continued

CF mutations and associated amplification primers

| CF Mutation Nucleotide Change | CF Mutation Nucleotide Change (HGVS nomenclature)* | CF Mutation Amino Acid Change | CF Mutation Amino Acid Change (HGVS nomenclature)* | Forward and Reverse PCR Amplification Primers |
|---|---|---|---|---|
| 574A > T | c.442A > T | I148F | p.Ile148Phe | q4e1F (SEQ ID NO: 9) and q4e1R (SEQ ID NO: 10) |
| 3704T > C | c.3572T > C | M1191T | p.Met1191Thr | q19e3F (SEQ ID NO: 37) and q19e4R (SEQ ID NO: 38) |
| 1248 + 5T > C (T in the splice donor site of intron 7, 5 nucleotides downstream of position 1248, is substituted with C) | c.1116 + 5T > C | | | q7e3F (SEQ ID NO: 17) and q7e4R (SEQ ID NO: 18) |
| 296 + 12T > G (T in intron 2, 12 nucleotides downstream of position 296, is substituted with G) | c.164 + 12T > G | | | q2e2F (SEQ ID NO: 5) and q2e2R (SEQ ID NO: 6) |
| 3849 + 3G > A (G in the splice donor site of intron 19, 3 nucleotides downstream of position 3849, is substituted with A) | c.3717 + 3G > A | | | q19e3F (SEQ ID NO: 37) and q19e4R (SEQ ID NO: 38) |
| 497A > G | c.365A > G | Y122C | p.Tyr122Cys | q4e1F (SEQ ID NO: 9) and q4e1R (SEQ ID NO: 10) |
| −141C > A | c.−274C > A | | | q-promoter-2-1F (SEQ ID NO: 3) and q-promoter-2-1R (SEQ ID NO: 4) |
| 2875G > C | c.2743G > C | V915L | p.Val915Leu | q15e3F (SEQ ID NO: 29) and q15e4R (SEQ ID NO: 30) |
| 2689A > G | c.2557A > G | I853V | p.Ile953Val | q14ae5F (SEQ ID NO: 25) and q14ae6R (SEQ ID NO: 26) |
| 3039A > G | c.2907A > G | A969A | 2nd last nucleotide in exon 15; no change to p.Ala969 | q15e3F (SEQ ID NO: 29) and q15e4R (SEQ ID NO: 30) |
| 405G > C | c.273G > C | G91G | Last nucleotide in exon 3; no change to p.Gly91. | s3e1F (SEQ ID NO: 7) and s3e2R (SEQ ID NO: 8) |
| 886G > A | c.754G > A | A252T | p.Ala252Thr | q6be2F (SEQ ID NO: 15) and q6be2R (SEQ ID NO: 16) |
| 4445G > A | c.4313G > A | R1438Q | p.Arg1438Gln | q24e1F (SEQ ID NO: 41) and q24e1R (SEQ ID NO: 42) |
| −228G > C | c.−361G > C | | | q-promoter-2-1F (SEQ ID NO: 3) and q-promoter-2-1R (SEQ ID NO: 4) |
| −295C > T | c.−427C > T | | | q-promoter-1-1F (SEQ ID NO: 1) and q-promoter-1-1R (SEQ ID NO: 2) |
| −379delC (C at position −379 is deleted) | c.−512delC | | | q-promoter-1-1F (SEQ ID NO: 1) and q-promoter-1-1R (SEQ ID NO: 2) |
| −540A > G | | | | q-promoter-1-1F (SEQ ID NO: 1) and q-promoter-1-1R (SEQ ID NO: 2) |

*HGVS nomenclature is based on Human Genome Variation Society guidelines as adopted by Cystic Fibrosis Centre at the Hospital for Sick Children in Toronto, Canada and US Cystic Fibrosis Foundation, Bethesda, MD, USA Further information relating to the CF mutations and the CFTR gene are found in FIG. 1. The primers for amplifying segments of the CFTR gene may hybridize to coding or non-coding CFTR sequences under stringent conditions. Preferred primers are those that flank mutant CF sequences.

By "mutations of the CFTR gene" or "mutant CF sequence" is meant one or more CFTR nucleic acid sequences that are associated or correlated with cystic fibrosis. The CF mutations disclosed in Table 1 may be correlated with a carrier state, or with a person afflicted with CF. Thus, the nucleic acid may be tested for any CF mutation described in Table 1. The nucleic acid sequences containing CF mutations are preferably DNA sequences, and are preferably genomic DNA sequences; however, RNA sequences such as mRNA or hnRNA may also contain nucleic acid mutant sequences that are associated with cystic fibrosis.

By "carrier state" is meant a person who contains one CFTR allele that is a mutant CF nucleic acid sequence, but a second allele that is not a mutant CF nucleic acid sequence. CF is an "autosomal recessive" disease, meaning that a mutation produces little or no phenotypic effect when present in a heterozygous condition with a non-disease related allele, but produces a "disease state" when a person is homozygous, i.e., both CFTR alleles are mutant CF nucleic acid sequences.

By "primer" is meant a sequence of nucleic acid, preferably DNA, that hybridizes to a substantially complementary target sequence and is recognized by DNA polymerase to begin DNA replication.

By "substantially complementary" is meant that two sequences hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

By "flanking" is meant that a primer hybridizes to a target nucleic acid adjoining a region of interest sought to be amplified on the target. The skilled artisan will understand that preferred primers are pairs of primers that hybridize upstream of a region of interest, one on each strand of a target double stranded DNA molecule, such that nucleotides may be added to the 3' end of the primer by a suitable DNA polymerase. Primers that flank mutant CF sequences do not actually anneal to the mutant sequence but rather anneal to sequence that adjoins the mutant sequence.

By "isolated" a nucleic acid (e.g., an RNA, DNA or a mixed polymer) is one which is substantially separated from other cellular components which naturally accompany such nucleic acid. The term embraces a nucleic acid sequence which has been removed from its naturally occurring environment, and includes recombinant or cloned DNA isolates, oligonucleotides, and chemically synthesized analogs or analogs biologically synthesized by heterologous systems.

By "substantially pure" a nucleic acid, represents more than 50% of the nucleic acid in a sample. The nucleic acid sample may exist in solution or as a dry preparation.

By "complement" is meant the complementary sequence to a nucleic acid according to standard Watson/Crick pairing rules. A complement sequence can also be a sequence of RNA complementary to the DNA sequence or its complement sequence, and can also be a cDNA.

By "coding sequence" is meant a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

By "non-coding sequence" is meant a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, etc.

Nucleic acid suspected of containing mutant CF sequences are amplified using one or more primers that flank the mutations under conditions such that the primers will amplify CFTR fragments containing the mutations, if present. The oligonucleotide sequences in Table 1 are useful for amplifying segments of the CFTR gene which contain the mutations in FIG. 1.

The method of identifying the presence or absence of mutant CF sequence by amplification can be used to determine whether a subject has a genotype containing one or more nucleotide sequences correlated with cystic fibrosis. The presence of a wildtype or mutant sequence at each predetermined location can be ascertained by the invention methods.

By "amplification" is meant one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods.

The nucleic acid suspected of containing mutant CF sequence may be obtained from a biological sample. By "biological sample" is meant a sample obtained from a biological source. A biological sample can, by way of non-limiting example, consist of or comprise blood, sera, urine, feces, epidermal sample, skin sample, cheek swab, sperm, amniotic fluid, cultured cells, bone marrow sample and/or chorionic villi. Convenient biological samples may be obtained by, for example, scraping cells from the surface of the buccal cavity. The term biological sample includes samples which have been processed to release or otherwise make available a nucleic acid for detection as described herein. For example, a biological sample may include a cDNA that has been obtained by reverse transcription of RNA from cells in a biological sample.

By "subject" is meant a human or any other animal which contains a CFTR gene that can be amplified using the primers and methods described herein. A subject can be a patient, which refers to a human presenting to a medical provider for diagnosis or treatment of a disease. A human includes pre and post natal forms. Particularly preferred subjects are humans being tested for the existence of a CF carrier state or disease state.

By "identifying" with respect to an amplified sample is meant that the presence or absence of a particular nucleic acid amplification product is detected. Numerous methods for detecting the results of a nucleic acid amplification method are known to those of skill in the art.

Specific primers may be used to amplify segments of the CFTR gene that are known to contain mutant CF sequence.

By amplifying specific regions of the CFTR gene, the primers facilitate the identification of wildtype or mutant CF sequence at a particular location of the CFTR gene. Primers for amplifying various regions of the CFTR gene include the following: SEQ ID NO 1: (q-promoter-1-1F) TGTAAAAC-GACGGCCAGTcgtgtcctaagatttctgtg and SEQ ID NO 2: (q-promoter-1-1R) CAGGAAACAGCTATGACCCTTTC-CCGATTCTGACTC are preferably used together as forward (F) and reverse (R) primers; SEQ ID NO 3: (q-promoter-2-1F) TGTAAAACGACGGCCAGTtgccaactggacctaaag and SEQ ID NO 4: (q-promoter-2-1R) CAGGAAACAGCTAT-GACCCAAACCCAACCCATACAC are preferably used together as forward (F) and reverse (R) primers; SEQ ID NO 5: (q2e2F) TGTAAAACGACGGCCAGTcataattttc-catatgccag and SEQ ID NO 6: (q2e2R) CAGGAAACAGC-TATGACCTATGTTTGCTTTCTCTTCTC are preferably used together as forward (F) and reverse (R) primers; SEQ ID NO 7: (s3e1F) TGTAAAACGACGGCCAGTcttgggt-taatctccttgga and SEQ ID NO 8: (s3e2R) CAGGAAACAGC-TATGACCATTCACCAGATTTCGTAGTC are preferably used together as forward (F) and reverse (R) primers; SEQ ID NO 9: (q4e1F) TGTAAAACGACGGCCAGTaaagtettgt-gagaaanctcagg and SEQ ID NO 10: (q4e1R) CAGGAAA-CAGCTATGACCCAGCTCACTACCTAATTTATGACAT are preferably used together as forward (F) and reverse (R) primers; SEQ ID NO 11: (g5e3F) TGTAAAACGACGGC-CAGTacatttatgaacctgagaag and SEQ ID NO 12: (g5e4R) CAGGAAACAGCTATGACCCAGAATAGG-GAAGCTAGAG are preferably used together as forward (F) and reverse (R) primers; SEQ ID NO 13: (q6ae1F) TGTAAAACGACGGCCAGTggggtggaagatacaatgac and SEQ ID NO 14: (q6ae1R) CAGGAAACAGCTATGAC-CCATAGAGCAGTCCTGGTMAC are preferably used together as forward (F) and reverse (R) primers; SEQ ID NO 15: (q6be2F) TGTAAAA CGACGGCCAGTaaaataatgc-ccatctgttg and SEQ ID NO 16: (q6be2R) CAGGAAACAGC-TATGACCGTGGAAGTCTACCATGATAAACATA are preferably used together as forward (F) and reverse (R) primers; SEQ ID NO 17: (q7e3F) TGTAAAACGACGGC-CAGTcttccattccaagatccc and SEQ ID NO 18: (q7e4R) CAG-GAAACAGCTATGACCGCAAAGTTCATTAGAACTGATC are preferably used together as forward (F) and reverse (R) primers; SEQ ID NO 19: (g9e9F) TGTAAAACGACGGC-CAGTtggatcatgggccatgtgc and SEQ ID NO 20: (g9e 11R) CAGGAAACAGCTATGACCAAAGAGA-CATGGACACCAAATTAAG are preferably used together as forward (F) and reverse (R) primers; SEQ ID NO 21: (q13-1e1F) TGTAAAACGACGGCCAGTcgag-gataaatgatttgctcaaag and SEQ ID NO 22: (q13-1e2R) CAG-GAAACAGCTATGACCTCGTATAGAGT-TGATTGGATTGAGA are preferably used together as forward (F) and reverse (R) primers; SEQ ID NO 23: (q13-2e1F) TGTAAAACGACGGCCAGTccctaactgagaccttacac and SEQ ID NO 24: (q13-2e1R) CAGGAAACAGCTAT-GACCTTCTGTGGGGTGAAATAC are preferably used together as forward (F) and reverse (R) primers; SEQ ID NO 25: (q14ae5F) TGTAAAACGACGGCCAGTgtggcat-gaaaecgtactgt and SEQ ID NO 26: (q14ae6R) CAGGAAA-CAGCTATGACCACATCCCCAAACTATCTTAA are preferably used together as forward (F) and reverse (R) primers; SEQ ID NO 27: (q14be2F) TGTAAAACGACGGCCAG-Tatgggaggaataggtgaaga and SEQ ID NO 28: (q14be2R) CAGGAAACAGCTATGACCTGGATTA-CAATACATACAAACA are preferably used together as forward (F) and reverse (R) primers; SEQ ID NO 29: (q15e3F) TGTAAAACGACGGCCAGTggttaagggtgcatgctcttc and SEQ ID NO 30: (q15e4R) CAGGAAACAGCTATGACCG-GCCCTATTGATGGTGGATC are preferably used together as forward (F) and reverse (R) primers; SEQ ID NO 31: (q17ae1F) TGTAAAACGACGGCCAGTacactttgtccactttgc and SEQ ID NO 32: (q17ae1R) CAGGAAACAGCTAT-GACCAGATGAGTATCGCACATTC are preferably used together as forward (F) and reverse (R) primers; SEQ ID NO 33: (q17be1F) TGTAAAACGACGGCCAGTatctat-tcaaagaatggcac and SEQ ID NO 34: (q17be 1R) CAGGAAA-CAGCTATGACCGATAACCTATAGAATGCAGC are preferably used together as forward (F) and reverse (R) primers; SEQ ID NO 35: (q18e1F) TGTAAAACGACGGCCAGTta-gatgctgtgatgaactg and SEQ ID NO 36: (q18e1R) CAG-GAAACAGCTATGACCGAAGGAAAGAAGAGATAAGG are preferably used together as forward (F) and reverse (R) primers; SEQ ID NO 37: (q19e3F) TGTAAAACGACGGC-CAGTcccgacaaataaccaagtgac and SEQ ID NO 38: (q19e4R) CAGGAAACAGCTATGACCGCTAACACAT-TGCTTCAGGCTAC are preferably used together as forward (F) and reverse (R) primers; SEQ ID NO 39: (q22e1F) TGTAAAACGACGGCCAGTctgtcaaggttgtaaatagac and SEQ ID NO 40: (q22e1R) CAGGAAACAGCTATGAC-CAAGCAGGCATAATGATFC are preferably used together as forward (F) and reverse (R) primers; SEQ ID NO 41: (q24e1F) TGTAAAACGACGGCCAGTtattttcctttgagcctg and SEQ ID NO 42: (q24e1R) CAGGAAACAGCTATGAC-CGCAGAGGTAACTGTTCCAC are preferably used together as forward (F) and reverse (R) primers. These pairs of primers, which may be used in multiplex amplifications, can amplify the regions of the CFTR gene shown in Table 2.

TABLE 2

CFTR Primer Pairs and Amplicon Characteristics

| Forward Primer | Reverse Primer | Exon/Intron | Size (in base pairs) |
|---|---|---|---|
| q-promoter-1-1F (SEQ ID NO: 1) | q-promoter-1-1R (SEQ ID NO: 2) | qp1 | 553 |
| q-promoter-2-1F (SEQ ID NO: 3) | q-promoter-2-1R (SEQ ID NO: 4) | qp2 | 634 |
| q2e2F (SEQ ID NO: 5) | q2e2F (SEQ ID NO: 6) | exon 2 | 323 |
| s3e1F (SEQ ID NO: 7) | s3e2R (SEQ ID NO: 8) | exon 3 | 345 |
| q4e1F (SEQ ID NO: 9) | q4e1R (SEQ ID NO: 10) | exon 4 | 413 |
| g5e3F (SEQ ID NO: 11) | g5e4R (SEQ ID NO: 12) | intron 5 | 425 |
| q6ae1F (SEQ ID NO: 13) | q6ae1R (SEQ ID NO: 14) | exon 6a | 334 |
| q6be2F (SEQ ID NO: 15) | q6be2R (SEQ ID NO: 16) | exon 6b | 341 |
| q7e3F (SEQ ID NO: 17) | q7e4R (SEQ ID NO: 18) | exon 7 | 431 |
| g9e9F (SEQ ID NO: 19) | g9e11R (SEQ ID NO: 20) | exon 9 | 396 |
| q13-1e1F (SEQ ID NO: 21) | q13-1e2R (SEQ ID NO: 22) | exon 13-1 | 355 |
| q13-2e1F (SEQ ID NO: 23) | q13-2e1R (SEQ ID NO: 24) | exon 13-2 | 584 |
| q14ae5F (SEQ ID NO: 25) | q14ae6R (SEQ ID NO: 26) | exon 14a | 281 |
| q14be2F (SEQ ID NO: 27) | q14be2R (SEQ ID NO: 28) | exon 14b | 223 |
| q15e3F (SEQ ID NO: 29) | q15e4R (SEQ ID NO: 30) | exon 15 | 471 |
| q17ae1F (SEQ ID NO: 31) | q17ae1R (SEQ ID NO: 32) | exon 17a | 280 |
| q17be1F (SEQ ID NO: 33) | q17be1R (SEQ ID NO: 34) | exon 17b | 504 |
| q18e1F (SEQ ID NO: 35) | q18e1R (SEQ ID NO: 36) | exon 18 | 471 |
| q19e3F (SEQ ID NO: 37) | q19e4R (SEQ ID NO: 38) | exon 19 | 489 |

TABLE 2-continued

CFTR Primer Pairs and Amplicon Characteristics

| Forward Primer | Reverse Primer | Exon/Intron | Size (in base pairs) |
|---|---|---|---|
| q22e1F (SEQ ID NO: 39) | q22e1R (SEQ ID NO: 40) | exon 22 | 446 |
| q24e1F (SEQ ID NO: 41) | q24e1R (SEQ ID NO: 42) | exon 24 | 426 |

If heterozygous polymorphism or mutation is present in one of the amplicons for exon 6b, the frameshift caused by the polymorphism or mutation will result in unreadable nucleotide sequences. Therefore, if a base change is detected in any one of these amplicons, sequencing should be performed to verify the sequence of another strand using an appropriate primer. This verification sequencing can be performed using the same PCR cleanup product as template. The verification sequencing primer for exon 6b is reflex6be1F (SEQ ID NO: 43): TTGATTGATTGATTGATTGATTT.

The nucleic acid to be amplified may be from a biological sample such as an organism, cell culture, tissue sample, and the like. The biological sample can be from a subject which includes any eukaryotic organism or animal, preferably fungi, invertebrates, insects, arachnids, fish, amphibians, reptiles, birds, marsupials and mammals. A preferred subject is a human, which may be a patient presenting to a medical provider for diagnosis or treatment of a disease. The biological sample may be obtained from a stage of life such as a fetus, young adult, adult, and the like. Particularly preferred subjects are humans being tested for the existence of a CF carrier state or disease state.

The sample to be analyzed may consist of or comprise blood, sera, urine, feces, epidermal sample, skin sample, cheek swab, sperm, amniotic fluid, cultured cells, bone marrow sample and/or chorionic villi, and the like. A biological sample may be processed to release or otherwise make available a nucleic acid for detection as described herein. Such processing may include steps of nucleic acid manipulation, e.g., preparing a cDNA by reverse transcription of RNA from the biological sample. Thus, the nucleic acid to be amplified by the methods of the invention may be DNA or RNA.

Nucleic acid may be amplified by one or more methods known in the art for copying a target nucleic acid, thereby increasing the number of copies of a selected nucleic acid sequence. Amplification may be exponential or linear. The sequences amplified in this manner form an "amplicon." In a preferred embodiment, the amplification is performed by the polymerase chain reaction ("PCR") (e.g., Mullis, K. et al., Cold Spring Harbor Symp. Quant. Biol. 51:263-273 (1986); Erlich H. et al., European Patent Application. 50,424; European Patent Application. 84,796, European Patent Application 258,017, European Patent Application. 237,362; Mullis, K., European Patent Application. 201,184; Mullis K. et al., U.S. Pat. No. 4,683,202; Erlich, H., U.S. Pat. No. 4,582,788; and Saiki, R. et al., U.S. Pat. No. 4,683,194). Other known nucleic acid amplification procedures that can be used include, for example, transcription-based amplification systems or isothermal amplification methods (Malek, L. T. et al., U.S. Pat. No. 5,130,238; Davey, C. et al., European Patent Application 329,822; Schuster et al., U.S. Pat. No. 5,169,766; Miller, H. I. et al., PCT application. WO 89/06700; Kwoh, D. et al., Proc. Natl. Acad. Sci. (U.S.A.) 86:1173 (1989); Gingeras, T. R. et al., PCT application WO 88/10315; Walker, G. T. et al., Proc. Natl. Acad. Sci. (U.S.A.) 89:392-396 (1992)). Amplification may be performed with relatively similar levels of each primer of a primer pair to generate a double stranded amplicon. However, asymmetric PCR may be used to amplify predominantly or exclusively a single stranded product as is well known in the art (e.g., Poddar et al. Molec. And Cell. Probes 14:25-32 (2000)). This can be achieved for each pair of primers by reducing the concentration of one primer significantly relative to the other primer of the pair (e.g. 100 fold difference). Amplification by asymmetric PCR is generally linear. One of ordinary skill in the art would know that there are many other useful methods that can be employed to amplify nucleic acid with the invention primers (e.g., isothermal methods, rolling circle methods, etc.), and that such methods may be used either in place of or together with, PCR methods. Persons of ordinary skill in the art also will readily acknowledge that enzymes and reagents necessary for amplifying nucleic acid sequences through the polymerase chain reaction, and techniques and procedures for performing PCR, are well known. The examples below illustrate a standard protocol for performing PCR and the amplification of nucleic acid sequences that correlate with or are indicative of cystic fibrosis.

In another aspect, the present invention provides methods of detecting a cystic fibrosis genotype in a biological sample. The methods comprise amplifying nucleic acids in a biological sample of the subject and identifying the presence or absence of one or more mutant cystic fibrosis nucleic acid sequences in the amplified nucleic acid. Accordingly, the present invention provides a method of determining the presence or absence of one or more mutant cystic fibrosis nucleic acid sequences in a nucleic acid containing sample, comprising: contacting the sample with reagents suitable for nucleic acid amplification including one or more pairs of nucleic acid primers flanking one or more predetermined nucleic acid sequences that are correlated with cystic fibrosis, amplifying the predetermined nucleic acid sequence(s), if present, to provide an amplified sample; and identifying the presence or absence of mutant or wild type sequences in the amplified sample.

One may analyze the amplified product for the presence of absence of any of a number of mutant CF sequences that may be present in the sample nucleic acid. As already discussed, numerous mutations in the CFTR gene have been associated with CF carrier and disease states. For example, a three base pair deletion leading to the omission of a phenylalanine residue in the gene product has been determined to correspond to the mutations of the CF gene in approximately 50% of Caucasian patients affected by CF. The table below identifies preferred CF sequences and identifies which of the primer pairs of the invention may be used to amplify the sequence.

The CF mutations described herein also may be detected in conjunction with other CF mutations known in the art. Such additional CF mutations include, for example, those known under symbols: 2789+5G>A; 711+1G>T; W1282X; 3120+1G>A; dI507; dF508; (F508C, 1507V, 1506V); N1303K; G542X, G551D, R553X, R560T, 1717-1G>A: R334W, R347P, 1078delT; R117H, I148T, 621+1G>T; G85E; R1162X, 3659delC; 2184delA; A455E, (5T, 7T, 9T); 3849+10kbC>T; and 1898+1G>A. Additional CF mutations were disclosed in U.S. application Ser. No. 11/074,903 filed Mar. 7, 2005, such as 605G→C, 1198-1203del/1204G→A (deletes TGGGCT and replaces G with A at position 1204), 1484G→T, 1573A→G, 1604G→C, 1641-1642AG→T, 2949-2953del (deletes TACTC), 2978A→T, 3239C→A, and 3429C→A, which are hereby incorporated by reference in their entirety. Any and all of these mutations can be detected using nucleic acid amplified with the invention primers as described herein or other suitable primers.

CF mutations in the amplified nucleic acid may be identified in any of a variety of ways well known to those of ordinary skill in the art. For example, if an amplification product is of a characteristic size, the product may be detected by examination of an electrophoretic gel for a band at a precise location. In another embodiment, probe molecules that hybridize to the mutant or wild type CF sequences can be used for detecting such sequences in the amplified product by solution phase or, more preferably, solid phase hybridization. Solid phase hybridization can be achieved, for example, by attaching the CF probes to a microchip. Probes for detecting CF mutant sequences are well known in the art.

CF probes for detecting mutations as described herein may be attached to a solid phase in the form of an array as is well known in the art (see, U.S. Pat. Nos. 6,403,320 and 6,406,844). For example, the full complement of 24 probes for CF mutations with additional control probes (30 in total) can be conjugated to a silicon chip essentially as described by Jenison et al., Biosens Bioelectron. 16(9-12):757-63 (2001) (see also U.S. Pat. Nos. 6,355,429 and 5,955,377). Amplicons that hybridized to particular probes on the chip can be identified by transformation into molecular thin films. This can be achieved by contacting the chip with an anti-biotin antibody or streptavidin conjugated to an enzyme such as horseradish peroxidase. Following binding of the antibody (or streptavidin)-enzyme conjugate to the chip, and washing away excess unbound conjugate, a substrate can be added such as tetramethvlbenzidine (TMB) {3,3',5,5'Tetramethylbenzidine} to achieve localized deposition (at the site of bound antibody) of a chemical precipitate as a thin film on the surface of the chip. Other enzyme/substrate systems that can be used are well known in the art and include, for example, the enzyme alkaline phosphatase and 5-bromo-4-chloro-3-indolyl phosphate as the substrate. The presence of deposited substrate on the chip at the locations in the array where probes are attached can be read by an optical scanner. U.S. Pat. Nos. 6,355,429 and 5,955,377, which are hereby incorporated by reference in their entirety including all charts and drawings, describe preferred devices for performing the methods of the present invention and their preparation, and describes methods for using them.

The binding of amplified nucleic acid to the probes on the solid phase following hybridization may be measured by methods well known in the art including, for example, optical detection methods described in U.S. Pat. No. 6,355,429. In preferred embodiments, an array platform (see, e.g., U.S. Pat. No. 6,288,220) can be used to perform the methods of the present invention, so that multiple mutant DNA sequences can be screened simultaneously. The array is preferably made of silicon, but can be other substances such as glass, metals, or other suitable material, to which one or more capture probes are attached. In preferred embodiments, at least one capture probe for each possible amplified product is attached to an array. Preferably an array contains 10, more preferably 20, even more preferably 30, and most preferably at least 60 different capture probes covalently attached to the array, each capture probe hybridizing to a different CF mutant sequence. Nucleic acid probes useful as positive and negative controls also may be included on the solid phase or used as controls for solution phase hybridization.

Another approach is variously referred to as PCR amplification of specific alleles (PASA) (Sarkar, et al., 1990 *Anal. Biochem.* 186:64-68), allele-specific amplification (ASA) (Okayama, et al, 1989 *J. Lab, Clin. Med.* 114:105-113), allele-specific PCR (ASPCR) (Wu, et 1989 *Proc. Natl. Acad. USA.* 86:2757-2760), and amplification-refractory mutation system (ARMS) (Newton, et al, 1989 *Nucleic Acids Res.* 17:2503-2516). The method is applicable for single base substitutions as well as micro deletions/insertions. In general, two complementary reactions are used. One contains a primer specific for the normal allele and the other reaction contains a primer for the mutant allele (both have a common 2nd primer). One PCR primer perfectly matches one allelic variant of the target, but is mismatched to the other. The mismatch is located at/near the 3' end of the primer leading to preferential amplification of the perfectly matched allele. Genotyping is based on whether there is amplification in one or in both reactions. A band in the normal reaction only indicates a normal allele. A band in the mutant reaction only indicates a mutant allele. Bands in both reactions indicate a heterozygote. As used herein, this approach will be referred to as "allele specific amplification."

In yet another approach, restriction fragment length polymorphism (RFLP), which refers to the digestion pattern when various restriction enzymes are applied to DNA, is used. RFLP analysis can be applied to PCR amplified DNA to identify CF mutations as disclosed herein.

In still another approach, wild type or mutant CF sequence in amplified DNA may be detected by direct sequence analysis of the amplified products. A variety of methods can be used for direct sequence analysis as is well known in the art. See, e.g., The PCR Technique: DNA Sequencing (eds. James Ellingboe and Ulf Gyllensten) Biotechniques Press, 1992; see also "SCAIP" (single condition amplification/internal primer) sequencing, by Flanigan et al. Am J Hum Genet. 2003 April; 72(4):931-9. Epub 2003 Mar. 11. Direct sequencing of CF mutations is also described in Strom et al., 2003 *Genetics in Medicine* 5(1): 9-14.

In yet another approach for detecting wild type or mutant CF sequences in amplified DNA, single nucleotide primer extension or "SNuPE" is used. SNuPE can be performed as described in U.S. Pat. No. 5,888,819 to Goelet et al., U.S. Pat. No. 5,846,710 to Bajaj, Piggee, C. et al. Journal of Chromatography A 781 (1997), p. 367-375 ("Capillary Electrophoresis for the Detection of Known Point Mutations by Single-Nucleotide Primer Extension and Laser-Induced Fluorescence Detection"); Hoogendoorn, B. et al., Human Genetics (1999) 104:89-93, ("Genotyping Single Nucleotide Polymorphism by Primer Extension and High Performance Liquid Chromatography"); and U.S. Pat. No. 5,885,775 to Haff et al. (analysis of single nucleotide polymorphism analysis by mass spectrometry).

Another method for detecting CF mutations include the Luminex xMAP system which has been adapted for cystic fibrosis mutation detection by TM Bioscience and is sold commercially as a universal bead array (Tag-It™).

Still another approach for detecting wild type or mutant CF sequences in amplified DNA is the oligonucleotide ligation assay or "OLA" or "OL". The OLA uses two oligonucleotides which are designed to be capable of hybridizing to abutting sequences of a single strand of a target molecule. One of the oligonucleotides is biotinylated, and the other is detectably labeled. If the precise complementary sequence is found in a target molecule, the oligonucleotides will hybridize such that their termini abut, and create a ligation substrate that can be captured and detected. See e.g., Nickerson et al. (1990) Proc. Natl. Acad. Sci. U.S.A. 87:8923-8927, Landegren, U. et al. (1988) Science 241:1077-1080 and U.S. Pat. No. 4,998,617.

These above approaches for detecting wild type or mutant CF sequence in the amplified nucleic acid is not meant to be limiting, and those of skill in the art will understand that numerous methods are known for determining the presence or absence of a particular nucleic acid amplification product.

In another aspect the present invention provides kits for one of the methods described herein. The kit optionally contain buffers, enzymes, and reagents for amplifying the CFTR nucleic acid via primer-directed amplification. The kit also may include one or more devices for detecting the presence or absence of particular mutant CF sequences in the amplified nucleic acid. Such devices may include one or more probes that hybridize to a mutant CF nucleic acid sequence, which may be attached to a bio-chip device, such as any of those described in U.S. Pat. No. 6,355,429. The bio-chip device optionally has at least one capture probe attached to a surface on the bio-chip that hybridizes to a mutant CF sequence. In preferred embodiments the bio-chip contains multiple probes, and most preferably contains at least one probe for a mutant CF sequence which, if present, would be amplified by a set of flanking primers. For example, if five pairs of flanking primers are used for amplification, the device would contain at least one CF mutant probe for each amplified product, or at least five probes. The kit also preferably contains instructions for using the components of the kit.

The following examples serve to illustrate the present invention. These examples are in no way intended to limit the scope of the invention.

EXAMPLES

Example 1

Sample Collection and Preparation

Whole Blood:

5 cc of whole blood is collected in a lavender-top (EDTA) tube or yellow-top (ACD) tube. Green-top (Na Heparin) tubes are acceptable but less desirable. DNA is extracted from blood. 100 ng or more DNA is prepared in TE or sterile water.

Amniotic Fluid:

10-15 cc of Amniotic Fluid is collected in a sterile plastic container.

Cultured Cells:

Two T-25 culture flasks with 80-100% confluent growth may be used.

Chorionic Villi:

10-20 mg of Chorionic Villi are collected in a sterile container. 2-3 ml of sterile saline or tissue culture medium is added.

Transport:

Whole Blood, Amniotic Fluid, Cultured Cells and Chorionic Villi can be shipped at room temperature (18°-26° C.). Amniotic Fluid, Cultured Cells or Chorionic Villi preferably is used without refrigeration or freezing. Whole Blood and Extracted DNA can be shipped at 2°-10° C.

Storage:

Whole Blood, Amniotic Fluid and Extracted DNA are stored at 2°-10° C. Amniotic Fluid is stored at 2°-10° C. only after the aliquot is removed for culturing. Cultured Cells and Chorionic Villi are stored at room temperature (18°-26° C.).

Stability:

Whole Blood is generally stable for 8 days at room temperature (18°-26° C.) or 8 days refrigerated at 2°-10° C. Amniotic Fluid, Cultured Cells, and Chorionic Villi are generally processed to obtain DNA within 24 hours of receipt. Extracted DNA is stable for at least 1 year at 2°-10° C.

Example 2

Amplification from DNA

Polymerase chain reaction (PCR) primer pairs were designed using the CFTR gene sequences in EMBL/Genbank (Accession Nos. M55106-M55131). Each PCR primer for the 32 separate PCR reactions contains either an M13 forward linker sequence or an M13 reverse linker sequence as appropriate to allow universal sequence reaction priming. Individual PCR reactions are performed in 96-well microtiter plates under the same conditions for each amplicon. Subsequently, the PCR products are purified with the Millipore Montage™ PCR$_{96}$ Cleanup kit (Millipore, Bedford, Mass.) on a Beckman BioMek 2000 biorobot. Further details are provided in Strom et al., 2003 *Genetics in Medicine* 5(1):9-14.

In general, individual amplifications were prepared in a volume of 25 μl, which is added to the 96 well microtiter plates. Each amplification volume contained 2 μl of the nucleic acid sample (generally 10-100 ng of DNA), 19 μl of PCR-Enzyme Mix (PCR mix stock is prepared with 2.5 μl of 10×PCR buffer, 0.5 μl Hot Start Taq (Qiagen Inc., Cat No. 203205), 0.5 μl MgCl$_2$ (from 25 mM stock), PCR primers, and 0.2 μl of 25 mM dNTP). Master mix contained primers, Qiagen PCR buffer with MgCl$_2$, bovine serum albumin (BSA) (New England BioLabs, Cat no. B9001B), and dNTPs (Amersham Biosciences, Cat no. 27-2032-01).

The final concentration in the PCR for MgCl$_2$ was 2.0 mM, for BSA was 0.8 μg/μl, and for each dNTP was 0.2 mM. Primer final concentrations varied from about 1.2 μM to about 0.4 μM.

PCR was conducted using the following temperature profile: step 1: 96° C. for 15 minutes; step 2: 94° C. for 15 seconds; step 3: decrease at 0.5° C./second to 56° C.; step 4: 56° C. for 20 seconds; step 5: increase at 0.3° C./second to 72° C., step 6: 72° C. for 30 seconds; step 7: increase 0.5° C./second up to 94° C.; step 8: repeat steps 2 to 7 thirty three times; step 9: 72° C. for 5 minutes; step 10: 4° C. hold (to stop the reaction).

Example 3

Detection of CF Mutations

The purified PCR products were diluted to approximately 10 ng/μL and cycle sequencing reactions were performed with an ABI Prism Big Dye™ Terminator v3.0 cycle sequencing reaction kit (Applied Biosystems, Foster City, Calif.) according to the manufacturer's protocol. The DNA primers used for the sequencing reaction were M 13 forward and reverse primers. Big Dye™ Terminator reaction products were purified by ethanol precipitation and analyzed on an ABI Prism 3100 Genetic Analyzer. Sequences obtained were examined for the presence of mutations by using ABI SeqScape v2.0 software. Both strands of DNA were sequenced.

PCR reactions, purifications, and cycle sequencing reactions were performed in 96-well microtiter plates using biorobots to avoid errors introduced by manual setups. Loading of samples onto the capillary sequencer was also automated. One plate was generally sufficient to perform the entire sequencing reaction for a single patient. Theoretically, if all reactions were successful, the entire sequences for a single patient could be obtained in 24-48 hours after receipt of blood. In practice, however, one or more reactions may need to be repeated because of polymorphisms in intron 8 and 6a or failed reactions.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

SEQUENCE LISTING

```
<160> NUMBER OF SEQ ID NOS: 43

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtaaaacga cggccagtcg tgtcctaaga tttctgtg                              38

<210> SEQ ID NO 2
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caggaaacag ctatgaccct ttcccgattc tgactc                               36

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgtaaaacga cggccagttg ccaactggac ctaaag                               36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caggaaacag ctatgaccca aacccaaccc atacac                               36
```

```
<210> SEQ ID NO 5
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgtaaaacga cggccagtca taattttcca tatgccag                           38

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
caggaaacag ctatgaccta tgtttgcttt ctcttctc                           38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgtaaaacga cggccagtct tgggttaatc tccttgga                           38

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggaaacag ctatgaccat tcaccagatt tcgtagtc                           38

<210> SEQ ID NO 9
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgtaaaacga cggccagtaa agtcttgtgt tgaaattctc agg                     43

<210> SEQ ID NO 10
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caggaaacag ctatgaccca gctcactacc taatttatga cat                     43

<210> SEQ ID NO 11
<211> LENGTH: 38
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgtaaaacga cggccagtac atttatgaac ctgagaag                              38

<210> SEQ ID NO 12
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
caggaaacag ctatgaccca gaatagggaa gctagag                               37

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgtaaaacga cggccagtgg ggtggaagat acaatgac                              38

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caggaaacag ctatgaccca tagagcagtc ctggttttac                            40

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgacggccag taaaataatg cccatctgtt g                                     31

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caggaaacag ctatgaccgt ggaagtctac catgataaac ata                        43

<210> SEQ ID NO 17
<211> LENGTH: 36
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 17
tgtaaaacga cggccagtct tccattccaa gatccc                                    36

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caggaaacag ctatgaccgc aaagttcatt agaactgatc                                40

<210> SEQ ID NO 19
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tgtaaaacga cggccagttg gatcatgggc catgtgc                                   37

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
caggaaacag ctatgaccaa agagacatgg acaccaaatt aag                            43

<210> SEQ ID NO 21
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tgtaaaacga cggccagtcg aggataaatg atttgctcaa ag                             42

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
caggaaacag ctatgacctc gtatagagtt gattggattg aga                            43

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
```

-continued

```
primer

<400> SEQUENCE: 23
tgtaaaacga cggccagttc ctaactgaga ccttacac                                    38

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caggaaacag ctatgacctt ctgtggggtg aaatac                                      36

<210> SEQ ID NO 25
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgtaaaacga cggccagtgt ggcatgaaac tgtactgt                                    38

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caggaaacag ctatgaccac atccccaaac tatcttaa                                    38

<210> SEQ ID NO 27
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgtaaaacga cggccagtat gggaggaata ggtgaaga                                    38

<210> SEQ ID NO 28
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
caggaaacag ctatgacctg gattacaata catacaaaca                                  40

<210> SEQ ID NO 29
<211> LENGTH: 39
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 29
tgtaaaacga cggccagtgg ttaagggtgc atgctcttc        39

<210> SEQ ID NO 30
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caggaaacag ctatgaccgg ccctattgat ggtggatc        38

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
tgtaaaacga cggccagtac actttgtcca ctttgc        36

<210> SEQ ID NO 32
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
caggaaacag ctatgaccag atgagtatcg cacattc        37

<210> SEQ ID NO 33
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tgtaaaacga cggccagtat ctattcaaag aatggcac        38

<210> SEQ ID NO 34
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
caggaaacag ctatgaccga taacctatag aatgcagc        38

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgtaaaacga cggccagtta gatgctgtga tgaactg                                    37

<210> SEQ ID NO 36
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
caggaaacag ctatgaccga aggaaagaag agataagg                                   38

<210> SEQ ID NO 37
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tgtaaaacga cggccagtcc cgacaaataa ccaagtgac                                  39

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
caggaaacag ctatgaccgc taacacattg cttcaggcta c                               41

<210> SEQ ID NO 39
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tgtaaaacga cggccagtct gtcaaggttg taaatagac                                  39

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
caggaaacag ctatgaccaa gcaggcataa tgattc                                     36

<210> SEQ ID NO 41
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tgtaaaacga cggccagtta ttttcctttg agcctg                                     36

```
<210> SEQ ID NO 42
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
caggaaacag ctatgaccgc agaggtaact gttccac                              37

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ttgattgatt gattgattga ttt                                             23
```

What is clamed is:

1. A method of determining whether a human is predisposed to cystic fibrosis, comprising
   detecting in a nucleic acid sample obtained from said human a 2068G>T mutation in both alleles of the cystic fibrosis transmembrane regulatory (CFTR) gene, and
   determining that said human with the 2068G>T mutation in both alleles of the CFTR gene has a predisposition to cystic fibrosis, whereby said mutation in both alleles indicates a predisposition to cystic fibrosis.

2. The method of claim 1, comprising further determining the presence or absence of a second CFTR gene mutation selected from the group consisting of 2777insTG, 3443A>T, 2443delA, 3123-3125delGTT, 4177delG, 630delG, 1342-2A>G, 297-1G>A 3500-2A>T, 4375-2A>G, 3172-3174delTAC, 2902G>C, 4115T>C, 4185G>C, 520C>G, 842A>C, 4528G>T, 448A>G, 574A>T, 3704T>C, 1248+5T>C, 296+12T>G, 3849+3G>A, 497A>G, −141C>A, 2875G>C, 2689A>G, 3039A>G, 405G>C, 886G>A, 4445G>A, −228G>C, −295C>T, −379delC, and −540A>G.

3. The method of claim 1, wherein said 2068G>T mutation is assessed using genomic DNA.

4. The method of claim 1, wherein said 2068G>T mutation is detected by nucleic acid sequencing.

5. The method of claim 1, wherein said 2068G>T mutation is detected by allele specific amplification.

6. The method of claim 1, wherein said 2068G>T mutation is detected by primer extension.

7. The method of claim 1, wherein said 2068G>T mutation is detected by oligonucleotide ligation.

8. The method of claim 1, wherein said 2068G>T mutation is detected by hybridization with a detectably labeled probe.

9. The method of claim 1, wherein said 2068G>T mutation is detected by detecting a mutation in the encoded CFTR protein using an antibody with binding specificity for the mutated CFTR protein.

10. A method of identifying a human with an increased likelihood of having an offspring predisposed to cystic fibrosis, comprising
    detecting in a nucleic acid sample obtained from said human a 2068G>T mutation in at least one allele of a cystic fibrosis transmembrane regulatory (CFTR) gene in said sample, and
    determining that said human with the 2068G>T mutation in at least one allele has an increased likelihood of having an offspring predisposed to cystic fibrosis, whereby said mutation in at least one allele indicates an increased likelihood of having an offspring predisposed to cystic fibrosis.

11. The method of claim 10, comprising further determining the presence or absence of a second CFTR gene mutation selected from the group consisting of 2777insTG, 3443A>T, 2443delA, 3123-3125delGTT, 4177delG, 630delG, 1342-2A>G, 297-1G>A 3500-2A>T, 4375-2A>G, 3172-3174delTAC, 2902G>C, 4115T>C, 4185G>C, 520C>G, 842A>C, 4528G>T, 448A>G, 574A>T, 3704T>C, 1248+5T>C, 296+12T>G, 3849+3G>A, 497A>G, −141C>A, 2875G>C, 2689A>G, 3039A>G, 405G>C, 886G>A, 4445G>A, −228G>C, −295C>T, −379delC, and −540A>G.

12. The method of claim 10, wherein said 2068G>T mutation is assessed using genomic DNA.

13. The method of claim 10, wherein said 2068G>T mutation is detected by nucleic acid sequencing.

14. The method of claim 10, wherein said 2068G>T mutation is detected by allele specific amplification.

15. The method of claim 10, wherein said 2068G>T mutation is detected by primer extension.

16. The method of claim 10, wherein said 2068G>T mutation is detected by oligonucleotide ligation.

17. The method of claim 10, wherein said 2068G>T mutation is detected by hybridization with a detectably labeled probe.

18. The method of claim 10, wherein said 2068G>T mutation is detected by detecting a mutation in the encoded CFTR protein using an antibody with binding specificity for the mutated CFTR protein.

19. A method of determining the cystic fibrosis status of a human, comprising:
    (a) detecting in a nucleic acid sample obtained from said human a 2068G>T mutation in one or both alleles of the cystic fibrosis transmembrane regulatory (CFTR) gene, and
    (b) determining that said human
        (i) has cystic fibrosis or is predisposed to cystic fibrosis when the human is homozygous for the 2068G>T mutation in the CFTR gene, whereby said mutation in both alleles of the CFTR gene indicates the human has cystic fibrosis or is predisposed to cystic fibrosis, or
(ii) is a cystic fibrosis carrier when the human is heterozygous for the 2068G>T mutation in the CFTR gene, whereby said mutation in only one allele of the CFTR gene indicates the human is a cystic fibrosis carrier.

20. The method of claim 19, comprising further determining the presence or absence of a second CFTR gene mutation selected from the group consisting of 2777insTG, 3443A>T, 2443delA, 3123-3125delGTT, 4177delG, 630delG, 1342-2A>G, 297-1G>A 3500-2A>T, 4375-2A>G, 3172-3174delTAC, 2902G>C, 4115T>C, 4185G>C, 520C>G, 842A>C, 4528G>T, 448A>G, 574A>T, 3704T>C, 1248+5T>C, 296+12T>G, 3849+3G>A, 497A>G, −141C>A, 2875G>C, 2689A>G, 3039A>G, 405G>C, 886G>A, 4445G>A, −228G>C, −295C>T, −379delC, and −540A>G.

21. The method of claim 19, wherein said 2068G>T mutation is detected by assessing genomic DNA or cDNA.

22. The method of claim 19, wherein said 2068G>T mutation is detected by allele specific amplification.

23. The method of claim 19, wherein said 2068G>T mutation is detected by primer extension.

24. The method of claim 19, wherein said 2068G>T mutation is detected by oligonucleotide ligation.

25. The method of claim 19, wherein said 2068G>T mutation is detected by hybridization with a detectably labeled probe containing the mutant sequence.

26. The method of claim 19, wherein said 2068G>T mutation is detected by detecting a mutation in the encoded CFTR protein using an antibody with binding specificity for the mutated CFTR protein.

* * * * *